United States Patent [19]

Mueller

[11] 4,092,342

[45] May 30, 1978

[54] METHOD FOR RECOVERING ALKYLALUMINUM CHLORIDES

[75] Inventor: Karl Heinz Mueller, Werne, Germany

[73] Assignee: Schering Aktiengesellschaft, Berlin and Bergkamen, Germany

[21] Appl. No.: 772,578

[22] Filed: Feb. 28, 1977

[30] Foreign Application Priority Data

Jun. 23, 1976 Germany .......................... 2628191

[51] Int. Cl.$^2$ ............................................... C07F 5/06
[52] U.S. Cl. ................................................ 260/448 A
[58] Field of Search ................................... 260/448 A

[56] References Cited

U.S. PATENT DOCUMENTS

| | | | |
|---|---|---|---|
| 2,270,292 | 1/1942 | Grosse | 260/448 A |
| 2,996,529 | 8/1961 | Bos | 260/448 A |
| 3,124,604 | 3/1964 | Hüther | 260/48 A |
| 3,946,058 | 3/1976 | Malpass et al. | 260/448 A |

OTHER PUBLICATIONS

Zakharkin et al., Zh. Obsh. Khim. 31, 3662–3665 (1961).

*Primary Examiner*—Helen M. S. Sneed
*Attorney, Agent, or Firm*—Curtis, Morris & Safford

[57] ABSTRACT

What is disclosed is a method for recovering a product which is a dialkylaluminum chloride, an alkylaluminum dichloride, or a mixture thereof wherein said alkyl has from 1 to 6 carbon atoms, said product having a zinc concentration therein of less than 200 ppm, from a mixture of said dialkylaluminum chloride and soluble zinc compounds, which method comprises reacting said mixture with aluminum chloride under an inert atmosphere at a temperature up to about 150° C. and then distilling off said product.

2 Claims, No Drawings

METHOD FOR RECOVERING ALKYLALUMINUM CHLORIDES

The present invention relates to a method for the recovery of dialkylaluminum chloride and/or alkylaluminum dichloride having 1 to 6 carbon atoms in the alkyl groups and having a zinc concentration of less than 200 parts per million from a mixture of dialkylaluminum chloride and soluble zinc compounds, which mixture may also contain trialkylaluminum.

German patent publication DAS No. 1,159,447 describes a method for preparing dialkylzinc from trialkylaluminum and zinc chloride. The reaction takes place according to equation I:

$$2R_3Al + ZnCl_2 \rightarrow R_2Zn + 2R_2AlCl \qquad (I)$$

According to a process described in German patent publication DAS No. 1,493,222, zinc dust and an alkyl chloride can also be used, instead of zinc chloride. In this case, the reaction takes place according to equation II:

$$R_3Al + Zn + RCl \rightarrow R_2Zn + R_2AlCl \qquad (II)$$

In both processes, dialkylaluminum chloride is produced as a by-product. It is recommended to separate the dialkylzinc and the dialkylaluminum chloride by distillation. Although distillative separation is, basically, superior to all other methods, for example to those involving separation by selective complex formation, it nevertheless shows the disadvantage that it is practically impossible to recover a dialkylaluminum chloride having a concentration of less than 200 ppm of zinc, as is required for many uses to which the product is put. This is particularly the case when the product is used as a catalyst component, for example for the diethylaluminum chloride which appears as a by-product in the preparation of diethylzinc from triethylaluminum and zinc chloride.

In German patent publication DOS No. 2,525,120 it is taught that dialkylaluminum chlorides having a zinc concentration of 200 ppm or less can be obtained from a mixture of dialkylaluminum chlorides and soluble zinc compounds such as is formed in the preparation of dialkylzinc according to DAS No. 1,159,447 or No. 1,493,222, if the mixture is strongly heated in order selectively to pyrolyze the zinc-containing compounds and then the dialkylaluminum chloride is distilled off in higher purity.

This process nevertheless has the disadvantage that the mixture must be heated for a sufficiently long period of time at a temperature of about 150° C to 240° C., but the dialkylaluminum chloride also begins noticeably to decompose already at about 150° C. Further, it is disadvantageous that zinc is formed in the pyrolysis of dialkylzinc, which zinc tends to bake together and readily induces clogging.

The object of the present invention it is to avoid these disadvantages, to find a method which reduces the zinc content of alkylaluminum chlorides produced in the preparation of dialkylzinc, and in this way to obtain highly pure alkylaluminum chlorides which will meet the purity requirements for further technical uses, for example for the preparation of catalysts.

The object has been attained according to the present invention, in which a mixture of dialkylaluminum chloride and soluble zinc compounds, possibly also containing trialkylaluminum, is reacted with aluminum chloride under an inert atmosphere at temperatures up to about 150° C. and, subsequently, dialkylaluminum chloride and/or alkylaluminum dichloride are distilled off.

This process is very protective and gives very high yields. The reaction of mixtures of dialkylaluminum chloride and soluble zinc compounds, as well as optional trialkylaluminum, (which mixtures arise, for example, from distillation residues in the preparation of diethylzinc according to the process of DAS No. 1,159,447 or according to the process of DAS No. 1,493,222, after the diethylzinc is distilled from the reaction mixture), with aluminum chloride is suitably carried out between 20° C. and 150° C., preferably between 50° C. and 80° C. It may be assumed that the soluble zinc compounds which cannot be removed distillatively are converted into a chlorine-containing zinc compound, e.g. zinc chloride, by the process of the invention. If a mixture of dialkylaluminum chloride and dialkylzinc is involved, only so much aluminum chloride need be reacted that intermediary alkylaluminum dichloride is formed according to equation III:

$$R_2AlCl + AlCl_3 \rightarrow 2RAlCl_2 \qquad (III)$$

Presumably, then, the dialkylzinc is converted into a chlorine-containing zinc compound, for example into zinc chloride according to equation IV:

$$2RAlCl_2 + R_2Zn \rightarrow 2R_2AlCl + ZnCl_2 \qquad (IV)$$

If, in the preparation of the dialkylzinc according to DAS No. 1,159,447 or DAS No. 1,493,222, an excess of trialkylaluminum has been used, which can be advantageous, then the mixture after distillative removal of the dialkylzinc still contains trialkylaluminum in addition to dialkylaluminum chloride and soluble zinc compounds. In this case, so much aluminum chloride must be additionally reacted that all trialkylaluminum is converted into dialkylaluminum chloride according to equation V:

$$2R_3Al + AlCl_3 \rightarrow 3R_2AlCl \qquad (V)$$

According to the process of the present invention, however, so much still-additional aluminum chloride can be reacted that a part or all of the dialkylaluminum chloride is converted to alkylaluminum dichloride according to equation III.

The more alkylaluminum dichloride is formed, the easier and more rapid is the conversion of the soluble, non-distillatively removable, zinc compounds to chlorine-containing zinc compounds, for example zinc chloride. The performance of the process of the invention is the easiest and simplest if so much additional aluminum chloride is used that excess aluminum chloride can react with dialkylzinc according to overall equation VI:

$$2AlCl_3 + R_2Zn \rightarrow 2RAlCl_2 + ZnCl_2 \qquad (VI)$$

Thus, the process can be so directed according to the amount of aluminum chloride which is added that one can, according to choice, obtain either dialkylaluminum chloride or alkylaluminum dichloride or mixtures of both.

The distillative removal of the dialkylaluminum chloride and/or of the alkylaluminum dichloride can take place according to the present invention without a column. In certain cases, the help of a column may be suitable. Also, the distillation must be performed under an inert atmosphere, suitably under reduced pressure, so that the head temperature does not exceed about 150° C.

It is surprising that all the zinc remains in the distillation residue predominately in the form of zinc chloride, even on distillative removal of ethylaluminum dichloride. Namely, aluminum chloride, for example, has the property, on distillative removal of ethylaluminum dichloride, partially to be entrained therewith. The zinc chloride which remains in the distillation residue can be recovered. Alkylaluminum dichlorides, for example ethylaluminum dichloride, and mixtures of dialkylaluminum chlorides and alkylaluminum dichlorides, for example ethylaluminum sesquichloride, are compounds which are sought as much as the dialkylaluminum chlorides, for example diethylaluminum chloride. Their principal use is in the field of catalysis. For this purpose, a high purity is necessary. According to the need, alkylaluminum dichlorides can also be easily converted to dialkylaluminum chlorides by comproportionation with trialkylaluminum.

A better understanding of the present invention and of its many advantages will be had by referring to the following specific examples, given by way of illustration.

EXAMPLE 1

A filtered distillation residue, obtained in the preparation of diethylzinc according to the process of DAS No. 1,159,447 after the diethylzinc has been distilled off from the reaction mixture, was chosen as the starting product. The filtered distillation residue was a colorless clear liquid which in large part comprised diethylaluminum chloride and, in addition to 19.7% of Al and 27.7% of Cl, still contained 3.1% of soluble Zn. 83.5 g of this material were added to a 250 ml 3-necked flask equipped with a stirrer, a thermometer, and a reflux condenser. The entire system was kept under nitrogen at atmospheric pressure. 93.5 g of aluminum chloride were added to this material and the reaction mixture was heated. After the aluminum chloride had entirely dissolved at 60° C., the reaction mixture was distilled at a reduced pressure of about 20 mm Hg using a Claisen attachment. At a head temperature of 90° C. – 100° C., 153 g of colorless and clear distillate passed over. This corresponded to a yield of 86.4%. The distillate gave the following analysis:

| Al | 20.9% |
|---|---|
| Cl | 57.1% |
| Zn | <10 ppm |

The theoretical values for pure ethylaluminum dichloride are:
Al 21.3%
Cl 55.9%

EXAMPLE 2

As a starting material, a diethylaluminum chloride was chosen which, in addition to 20.7% of Al and 27.5% of Cl, still contained 3.0% of soluble Zn. 89 g of this material were, as described in Example 1, reacted with 92.5 g of aluminum chloride. After the aluminum chloride had dissolved, the reaction mixture was vacuum distilled as described in Example 1. At a head temperature of 93° C. to 101° C., 161 g of colorless and clear distillate passed over. This corresponded to a yield of 88.7%. The distillate showed the following analysis:

| Al | 21.1% |
|---|---|
| Cl | 54.3% |
| Zn | <100 ppm |

EXAMPLE 3

As a starting product, diethylaluminum chloride having a content of about 8% of triethylaluminum was chosen, which product still contained 2.5% of soluble zinc in addition to 20.9% of Al and 25.0% of Cl. 100 g of this material were added to a 500 ml 3-necked flask equipped with a stirrer, a thermometer, and a reflux condenser. The entire system was held under nitrogen at atmospheric pressure. This material was heated with stirring and, at 50° C. to 60° C., 128.9 g of aluminum chloride were added portion-wise. After the aluminum chloride had reacted, the reaction mixture was vacuum distilled as described in Example 1. At a head temperature of 94° C. to 103° C., 211.5 g of colorless and clear distillate passed over. This corresponds to a yield of 92.4%. The distillate showed the following analysis:

| Al | 21.0% |
|---|---|
| Cl | 56.3% |
| Zn | <10 ppm |

EXAMPLE 4

100 g of diethylaluminum chloride having a content of about 13% of triethylaluminum, and which still contained 0.4% of soluble Zn in addition to 22.3% of Al and 24.8% of Cl, was reacted with 49 g of aluminum chloride as described in Example 1. The reaction mixture was distilled at a reduced pressure of 280 – 215 mm Hg through a Claisen attachment. At a head temperature of 167° C. to 164° C., 140 g of colorless and clear distillate passed over. This corresponds to a yield of 94.0%. The distillate shows the following analysis:

| Al | 21.4% |
|---|---|
| Cl | 43.8% |
| Zn | <100 ppm. |

The theoretical values for ethylaluminum sesquichloride are:

| Al | 21.8% |
|---|---|
| Cl | 43.0% |

EXAMPLE 5

A mixture of about 88g of diethylaluminum chloride and about 12% of triethylaluminum, which contained about 0.1% of soluble Zn, was reacted with 11.9 g of aluminum chloride as described in Example 1. The reaction mixture was distilled at a reduced pressure of 180 to 105 mm Hg through a Claisen attachment. At a head temperature of 151° to 132° C., 104 g of a colorless and clear distillate passed over (yield: 92.9%). The distillate showed the following analysis:

| Al | 21.8% |
|---|---|
| Cl | 30.6% |

| | |
|---|---|
| Zn | <100 ppm. |

The theoretical values for diethylaluminum chloride are:

| | |
|---|---|
| Al | 22.4% |
| Cl | 29.4% |

EXAMPLE 6

As the starting material, a diisobutylaluminum chloride was chosen which, in addition to 14.5% Al and 19.2% Cl, still contained 1.5% of soluble Zn. 100 g of this material were, as described in Example 3, reacted with 81.1 g of aluminum chloride. The reaction mixture was distilled twice through a Claisen attachment, first at a reduced pressure of 10 mm Hg, then at a pressure of 0.1 mm Hg.

The yield for the first distillation was 95.0% (head temperature: 114° to 127° C.), and 96.5% for the second distillation (head temperature: 48° to 60° C.). In the latter distillate, Zn was no longer determinable. The analysis gave the following values:

| | |
|---|---|
| Al | 17.4% |
| Cl | 46.4% |

The theoretical values for isobutylaluminum dichloride are:

| | |
|---|---|
| Al | 17.4% |
| Cl | 45.8%. |

What is claimed is:

1. A method for recovering a product which is a dialkylaluminum chloride, an alkylaluminum dichloride, or a mixture thereof wherein said alkyl has from 1 to 6 carbon atoms, said product having a zinc concentration therein of less than 200 ppm, from a mixture of said dialkylaluminum chloride and soluble zinc compounds, which method comprises reacting said mixture with aluminum chloride under an inert atmosphere at a temperature up to about 150° C. and then distilling off said product.

2. A method as in claim 1 wherein said mixture additionally contains trialkylaluminum.

* * * * *